(12) United States Patent
Dupont et al.

(10) Patent No.: US 11,491,010 B2
(45) Date of Patent: Nov. 8, 2022

(54) OPTICAL DELIVERY AND INSERTION OF ARTIFICIAL CHORDAE TENDINEAE

(71) Applicant: Children's Medical Center Corporation, Boston, MA (US)

(72) Inventors: Pierre Dupont, Wellesley, MA (US); Karl D. Price, Brookline, MA (US); Gustavo Arnal, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/429,107

(22) PCT Filed: Feb. 10, 2020

(86) PCT No.: PCT/US2020/017446
§ 371 (c)(1),
(2) Date: Aug. 6, 2021

(87) PCT Pub. No.: WO2020/163852
PCT Pub. Date: Aug. 13, 2020

(65) Prior Publication Data
US 2022/0039956 A1 Feb. 10, 2022

Related U.S. Application Data

(60) Provisional application No. 62/802,739, filed on Feb. 8, 2019.

(51) Int. Cl.
*A61F 2/24* (2006.01)
*A61B 1/018* (2006.01)
(Continued)

(52) U.S. Cl.
CPC ............ *A61F 2/2466* (2013.01); *A61B 1/018* (2013.01); *A61B 1/06* (2013.01); *A61B 17/3421* (2013.01); *A61F 2/2457* (2013.01)

(58) Field of Classification Search
CPC ....... A61B 1/018; A61B 1/06; A61B 17/3421; A61B 17/00008; A61B 2017/00243; A61B 2017/320044; A61F 2/2466; A61F 2/2457
See application file for complete search history.

(56) References Cited

U.S. PATENT DOCUMENTS 7,635,386 B1    12/2009 Gammie
2003/0195529 A1  10/2003 Takamoto et al.
(Continued)

OTHER PUBLICATIONS

Machaidze, Z. et al., Optically-guided instrument for transapical beating-heart delivery of artificial mitral chordae tendineae. The Journal of Thoracic and Cardiovascular Surgery; Nov. 2019; 18 pages.
(Continued)

*Primary Examiner* — Ashley L Fishback
(74) *Attorney, Agent, or Firm* — Fish & Richardson P.C.

(57) ABSTRACT

The present disclosure involves a system and method of use for delivering an interventional instrument, such as an artificial chordae tendineae (ACT) delivery instrument, into a beating heart. By delivering interventional instruments in a beating heart via the system described here, complex and invasive open heart procedures as well as cardiopulmonary bypass can be avoided, significantly reducing patient trauma and recovery time as well as operation time and complexity. The system disclosed includes an optical imaging system to provide the practitioner with visual imagery from the end of the system, and allow for real-time or near real-time imaging of tissue inside the beating heart (e.g., leaflet tissue). This provides for accurate verification of placement of the interventional instrument. In addition, the system includes a grasping mechanism, which allows the practitioner to hold tissue in position prior to placing the interventional instrument.

24 Claims, 10 Drawing Sheets

(51) Int. Cl.
    *A61B 1/06*           (2006.01)
    *A61B 17/34*        (2006.01)

(56) References Cited

U.S. PATENT DOCUMENTS

| | | |
|---|---|---|
| 2005/0090709 A1* | 4/2005 | Okada .................... A61B 1/042 |
| | | 600/104 |
| 2007/0083217 A1* | 4/2007 | Eversull ................. A61B 1/053 |
| | | 606/114 |
| 2008/0306335 A1 | 12/2008 | Lau et al. |
| 2009/0131907 A1 | 5/2009 | Chin et al. |
| 2010/0042147 A1 | 2/2010 | Janovsky et al. |
| 2012/0184971 A1 | 7/2012 | Zentgraf et al. |
| 2014/0039324 A1 | 2/2014 | Speziali |
| 2014/0114404 A1 | 4/2014 | Gammie |
| 2016/0367120 A1 | 12/2016 | Dupont et al. |

OTHER PUBLICATIONS

International Search Report for PCT/US2020/17446 dated Apr. 30, 2020.
PCT International Preliminary Report on Patentability in International Appln. No. PCT/US2020/017446, dated Aug. 10, 2021, 8 pages.
Ramlawi et al., "Mitral valve surgery: current minimally invasive and transcatheter options," Methodist DeBakey Cardiovascular Journal, Jan. 2016, 12(1):20.
EP Extended Search Report in European Appln. No. 2075324.3, dated Oct. 4, 2022, 7 pages.

* cited by examiner

OPTICAL DELIVERY AND INSERTION OF ARTIFICIAL CHORDAE TENDINEAE

CROSS REFERENCE OF RELATED APPLICATIONS

This application is a U.S. National Phase application under 35 U.S.C. § 371 of International Patent Application No. PCT/US2020/017446, filed on Feb. 10, 2020, which claims priority to U.S. Application Ser. No. 62/802,739, filed on Feb. 8, 2019, the contents of both which are incorporated here by reference in their entirety.

This invention was made with government support under Grant Numbers HL124020 awarded by the National Institutes of Health. The Government has certain rights in the invention.

TECHNICAL FIELD

This disclosure generally relates to interventional instruments and methods of delivering interventional instruments into a beating heart.

BACKGROUND

Vascular heart disease is a health problem afflicting over 2.5% of the U.S. population. A variety of percutaneous and transcardiac procedures for valve replacement have been developed. Catheter-based interventions provide a relatively low-risk opportunity to intervene earlier in the disease process, as well as in the sickest patients, while avoiding the risks of cardiopulmonary bypass. Procedures that can be performed via catheter include transcatheter aortic valve replacement and catheter-delivered clips to reduce or eliminate mitral valve regurgitation. Beating-heart interventions provide the opportunity for continuous intra-operative assessment of the repair.

SUMMARY

This disclosure is based, at least in part, on the discovery that interventional procedures, such as intracardiac procedures, can be guided by imaging provided through an optical window integrated on the distal tip of a system to be inserted into an interventional site, such as into a beating heart. The system can provide a channel for delivery of instruments to the interventional site. Imaging at the interventional site (e.g., within the heart) before, during, and/or after a procedure provides for image-guided positioning of interventional instruments guided by or inserted through the system, such as an artificial chordae tendineae (ACT) delivery instrument, a mitral valve clip, or another instrument. Imaging at the interventional site can also facilitate detection of contact between the target tissue and the system or the instrument. In addition, the system described here provides one or more movable grasping fingers that can grasp the target tissue, e.g., to stabilize and control the position of the system or the instrument relative to the target tissue. The optical window at the distal tip of the system provides for image guidance for the grasping. Once the system or the instrument is positioned, procedures, such as procedures within the beating heart, can be carried out under image guidance, and the result of the procedure can be visualized in vivo and in real time. For instance, under image guidance, a mitral valve leaflet can be grasped by between the grasping finger and the optical window of the system to stabilize the position of the mitral valve leaflet for delivery of an anchor through the leaflet.

In an aspect, a system for delivering an interventional instrument into a beating heart includes a housing, wherein a first channel is defined through the housing, the first channel configured to receive the interventional instrument. The system includes a grasping finger disposed at a distal end of the housing. The system includes an optical finger, the optical finger including an optical window formed of a transparent material, wherein a second channel is defined through the optical window from a proximal face to a distal face of the optical window, wherein the second channel is aligned with the first channel through the housing; and an optical system positioned to obtain optical images of an area adjacent to the distal face of the optical window. The system is configured to take on an open configuration or a closed configuration, wherein a relative spacing between the distal face of the optical window and the grasping finger along an axis defined by the first channel is greater in the open configuration than in the closed configuration.

Embodiments can include any combination of one or more of the following features.

The optical system includes an imaging system positioned to obtain optical images of the area adjacent to the distal face of the optical window; and an illumination system configured to provide illumination to the area adjacent to the distal face of the optical window.

The optical system is disposed external to the optical window.

The optical system is embedded in the transparent material of the optical window.

The optical finger is translatable relative to the grasping finger along the axis defined by the first channel. The system includes a control tube rigidly connected to the optical finger. The control tube defines the first channel. The system includes a sheath, wherein a distal end of the sheath is connected to the housing, and wherein the control tube extends along at least a portion of a length of the sheath. The system includes a control handle configured to control a translation of the control tube along the axis defined by the first channel.

The grasping finger is fixed relative to the housing.

The grasping finger is translatable relative to the optical finger along the axis defined by the first channel. The system includes a control tube rigidly connected to the grasping finger. The optical finger is fixed relative to the housing.

The optical finger has a first diameter, and wherein the grasping finger has an inner diameter greater than the first diameter.

When the system is in the open position, the grasping finger is positioned distally forward of the distal face of the optical window along the axis.

When the system is in the closed position, the grasping finger is concentric with a cross-sectional plane of the optical window.

When the system is the closed position, the grasping finger is positioned distally forward of the distal face of the optical window along the axis.

When the system is in the closed position, the grasping finger is not present in a field of view of the optical system.

The grasping finger is attached to the housing by a support arm.

The system includes an elongated sheath, wherein the housing is attached to a distal end of the sheath.

The system includes a flexible catheter, wherein the housing is attached to a distal end of the catheter.

The grasping finger is rigidly affixed to the housing.

The system includes a first tube rigidly connected to the optical finger, the tube defining the first channel. The system includes a handle configured to cause translation of the first tube along the axis defined by the first channel. The system includes a second tube rigidly connected to the housing, wherein the first and second tubes are concentric. The system includes a handle configured to cause translation of the first tube relative to the second tube, translation of the second tube relative to the first tube, or both.

The transparent material is a compliant, silicone based material.

The optical window is a hollow optical window. The optical window is configured to expand when filled with a liquid.

The system includes an instrument for delivery of artificial chordae tendineae, wherein the instrument is sized to be inserted into the first and second channels. The instrument for delivery of artificial chordae tendineae (ACT) includes a stylet, configured to puncture a leaflet in a cardiac valve; an anchor, configured to pass through the leaflet and affix an ACT to the leaflet; and a delivery cannula, wherein the stylet, anchor, ACT, and delivery cannula are configured to pass through the first and second channel.

The system includes an intermediate grasping finger, wherein the intermediate grasping finger is positioned distal to the optical finger and proximal to the grasping finger when the system is in the open configuration. The intermediate grasping finger is translatable along the axis defined by the first channel. The intermediate grasping finger is translatable independent of translation of the optical finger and independent of translation of the grasping finger.

In an aspect, a method for delivering an interventional instrument into a beating heart includes inserting into a chamber of the beating heart, a delivery system including a housing, wherein a first channel is defined through the length of the housing, the first channel configured to receive the interventional instrument; a grasping finger disposed at a distal end of the housing; and an optical finger including an optical window formed of a transparent material. The method includes obtaining, by an optical system of the optical finger, optical images of an area adjacent to a distal face of the optical window; opening the delivery system into an open position, including increasing a relative spacing between the distal face of the optical window and the grasping finger along an axis defined by the first channel; and closing the delivery system into a closed position, including decreasing the relative spacing between the distal face of the optical window and the grasping finger.

Embodiments can include any combination of one or more of the following features.

Closing the delivery system includes decreasing the relative spacing until the grasping finger is concentric with a cross-sectional plane of the optical window.

Opening and closing the delivery system includes translating the optical finger relative to the grasping finger along the axis defined by the first channel. Translating the optical finger relative to the grasping finger includes moving a control tube along the axis defined by the first channel, the control tube rigidly connected to the optical finger. Translating the optical finger relative to the grasping finger includes moving the control tube relative to a second tube concentric with the control tube, the second tube rigidly connected to the housing.

Opening and closing the delivery system includes translating the grasping finger relative to the optical finger along the axis defined by the first channel.

The method includes inserting the interventional instrument through the first channel defined through the housing and through a second channel defined through the optical finger, wherein the first and second channels are aligned.

Closing the delivery system includes grasping a leaflet of a cardiac valve.

Inserting the delivery system into a chamber of the beating heart includes inserting the delivery system in a collapsed configuration. The method includes opening the delivery system into an expanded configuration after inserting the collapsed delivery system into the chamber of the beating heart. The method includes removing the delivery system from the chamber of the beating heart, including closing the delivery system into the collapsed configuration.

Other features and advantages of the invention will be apparent from the following detailed description and from the claims.

DETAILED DESCRIPTION

This disclosure describes a system (e.g., a catheter-based system) for delivering an interventional instrument, such as an artificial chordae tendineae (ACT) delivery instrument, into a beating heart. By delivering interventional instruments in a beating heart via the system described here, complex and invasive open heart procedures as well as cardiopulmonary bypass can be avoided, reducing patient trauma and recovery time as well as procedure time and complexity. The system disclosed includes an optical imaging system to provide the practitioner with visual imagery from the distal end of the system, which allows for real-time or near real-time imaging of tissue ahead of the distal end of the system, e.g., tissue inside the beating heart (e.g., mitral valve leaflet tissue). This image guidance can facilitate verification of placement of the system or verification of placement or delivery of the interventional instrument. In addition, the system includes a grasping mechanism, such as one or more moveable grasping fingers, which allows the practitioner to hold tissue in position, e.g., prior to placing the interventional instrument. In an example, the practitioner can verify the precise placement of an ACT delivery instrument with respect to the free edge of a leaflet of the mitral valve, which can help ensure accurate delivery of an ACT to the leaflet. In an example, the practitioner can precisely deliver multiple ACTs in the same leaflet relative to each other, because the previously delivered ACTs can be visually seen in the leaflet.

Figure 1A:
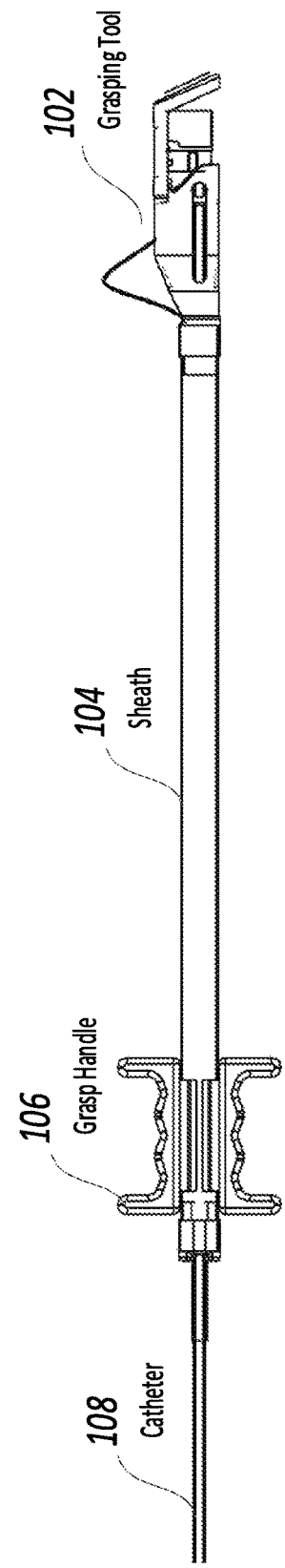
FIG. 1A depicts a high level view of a system for delivering interventional instruments.

FIG. 1A depicts a high level overview of an interventional instrument delivery system 100 having a grasping tool 102, a sheath 104, a grasp handle 106, and a catheter 108. The grasping tool 102 (described in greater detail below) is attached to a distal end of the sheath 104. The grasping tool 102 includes one or more moveable grasping fingers for grasping of tissue, and an optical window positioned to obtain optical images of the environment around the distal end of the grasping tool 102. The sheath 104 is an elongated, straight structure which provides mechanical support for the system 100. The sheath 104 can be formed from, e.g., a flexible plastic or polymer, a metal such as aluminum, stainless steel, or titanium, or other suitable materials. In some implementations the sheath 104 can be a flexible and/or steerable catheter, such that a practitioner can manipulate the shape and curvature of the sheath, e.g., for insertion of the system through a tubular structure of a patient, such as through a vein or artery. The sheath 104 can house one or more wires for transmitting or receiving electrical signals (e.g., to provide power or control signals to an optical system and/or to receive image data from the optical system). The sheath can define an instrument delivery channel for the interventional instrument (e.g., an ACT delivery instrument) to pass through. In some examples, the instrument delivery channel is defined by a tube (not shown) that connects to a component of the grasping tool 102 to provide control of the translation of the one or more grasping fingers of the grasping tool 102, as discussed further below.

Figure 1B:
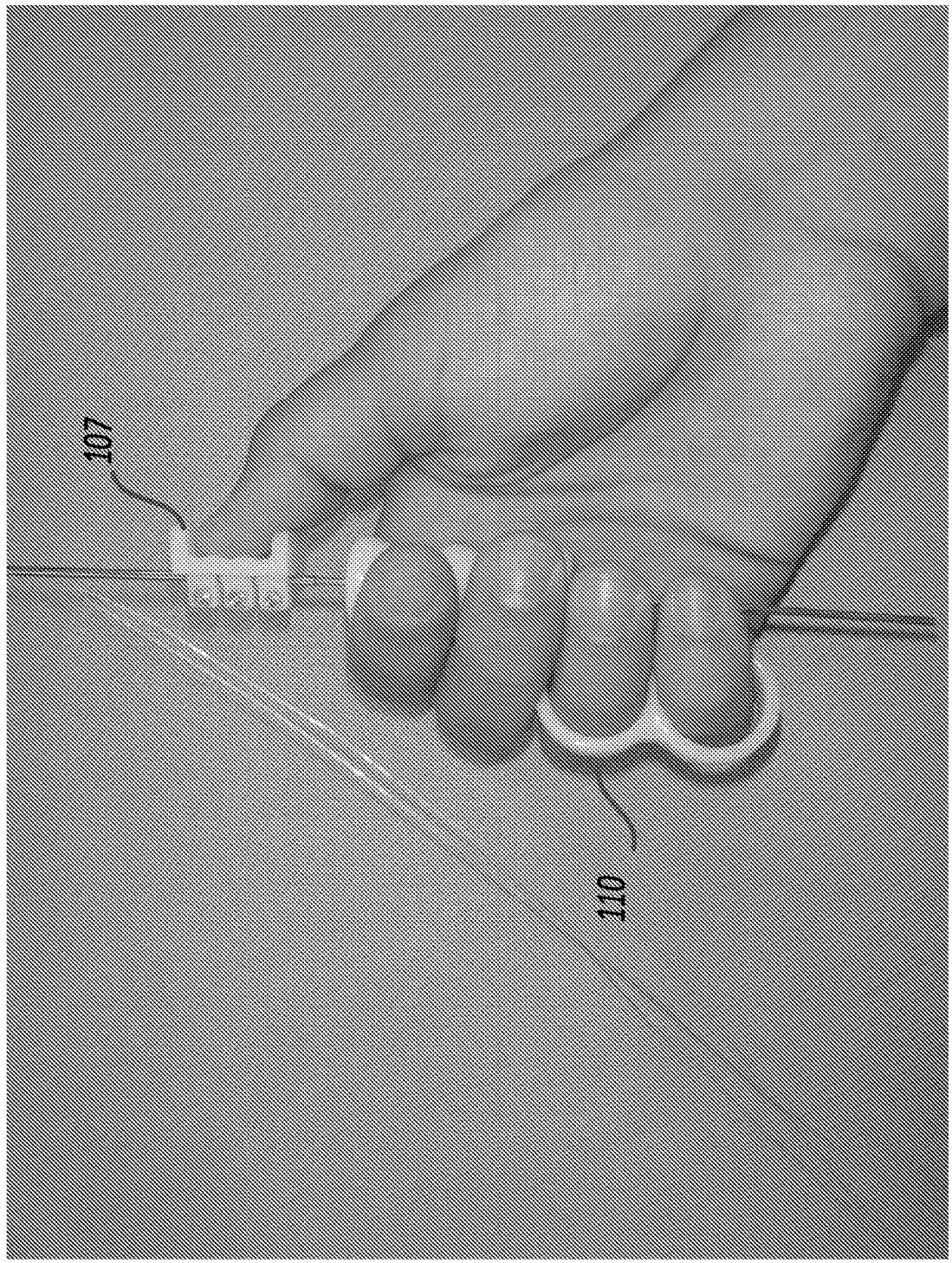
FIG. 1B depicts a grasp handle configuration for a system for delivering interventional instruments.

A grasp handle 106 is disposed at a proximal end of the sheath 104. The grasp handle 106 can provide a grip or handhold from which the practitioner can operate the interventional instrument delivery system 100. In some implementations, the grasp handle 106 includes a thumb actuator which can be used to control the operation of the one or more grasping fingers of the grasping tool 102. For instance, when the translation of the one or more grasping fingers is implemented by motion of a tube that defines the instrument delivery channel through the sheath, the grasp handle 106 is connected to the tube such that motion of the thumb actuator causes motion of the tube. FIG. 1B shows an example implementation of the grasp handle 106. As shown in FIG. 1B, the grasp handle 106 can include a thumb actuator 107 by which grasping action can be controlled, and a handhold 110 for secure handling of the delivery system.

A catheter 108 can be attached to the proximal end of the sheath 104, such that the entire system 100 defines or contains an instrument delivery channel that defines a pathway through which an interventional instrument can pass from the catheter 108, through the sheath 104 and to grasping tool 102, to be inserted into the beating heart of a patient. The catheter 108 can be a flexible or rigid catheter, and can be detachable from the sheath 104, e.g., to enable the rapid replacement of catheters or substitution of various additional implements into the interventional instrument delivery system 100.

Figure 2:
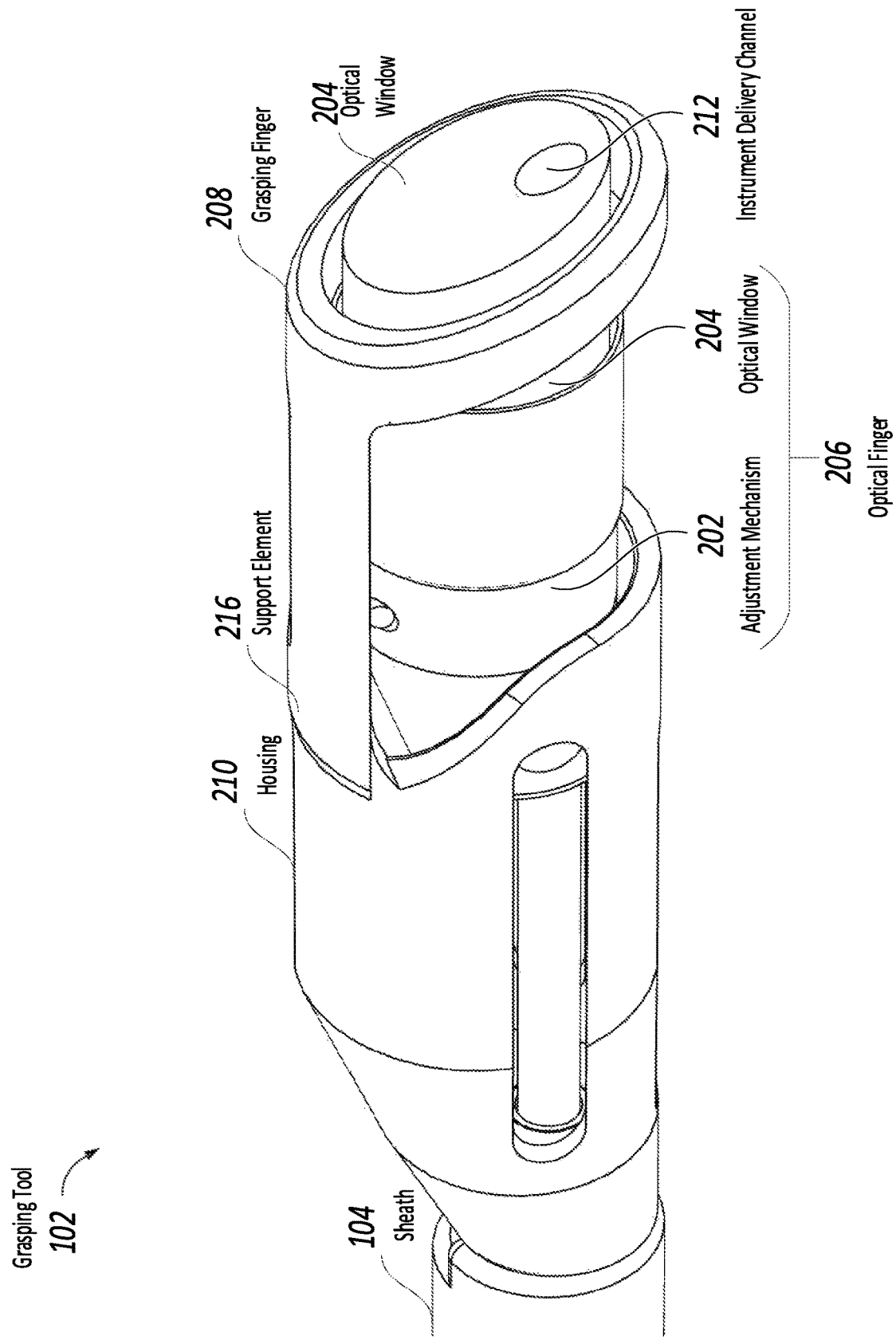
FIG. 2 is an isometric view of a system for delivering interventional instruments.

FIG. 2 is an isometric view of an example implementation of the grasping tool 102. The grasping tool 102 includes an optical finger 206, which includes an adjustment mechanism 202 and an optical window 204. The optical finger 206 also includes an optical system including an imaging system and illumination system (see FIGS. 3 and 4), among other things.

Relative motion between the optical finger 206 and a grasping finger 208 attached to a housing 210 of the grasping tool 102 enables the grasping tool 102 to grasp tissue disposed in the space between the distal face of the optical window 204 and the grasping finger 208. For instance, the adjustment mechanism 202 of the optical finger 206 can be attached to a first end of a tube (e.g., the tube defining the instrument delivery channel through the sheath 104, as discussed above). The tube can be translated proximally or distally along an axis defined by the length of the sheath 104 to cause the adjustment mechanism 202 (and thereby the entire optical finger 206) to move proximally or distally relative to the grasping finger 208. As discussed in more detail below, distal movement of the optical finger 206 toward the grasping finger 208 enables tissue to be grasped between the optical finger 206 and the grasping finger 208; proximal motion of the optical finger 206 away from the grasping finger 208 enables grasped tissue to be released. In some implementations, the optical finger 206 is fixed in place relative to the sheath and a grasping finger 208 (discussed below) moves relative to the optical finger 206. For instance, the grasping finger 208 can be attached to the tube defining the instrument delivery channel through the sheath 104. In some implementations, both the optical finger 206 and the grasping finger 208 can be moved.

The optical window 204 can be formed of a compliant, transparent material. By compliant, we mean solid, yet sufficiently flexible to conform to a surface or tissue that it comes into contact with. In some instances, compliance can be a measure of physical distortion per unit of strain an object undergoes. By transparent, we mean that at least some visible or infra-red light can be transmitted through the optical window 204, e.g., a sufficient amount of light to enable imaging of the environment in the vicinity of a distal face of the optical window 204. In some implementations, the optical window 204 is a solid material. In some implementations, the optical window 204 is a hollow polymer structure that is collapsible to enable intravascular delivery to and removal from an interventional site and expandable, e.g., inflatable by filling with air or liquid (e.g., saline) upon arrival at the interventional site. In some examples, the entire grasping tool 102 is collapsible to enable intravascular delivery and removal, and expandable to enable use upon arrival at the interventional site.

The optical window 204 includes an optical system including an imaging system, such as a camera or fiber optic cable, and an illumination system, such as a light emitting diode or fiber optic illumination. In some examples, the imaging system, the illumination system, or both are embedded in the transparent material of the solid optical window 204. In some examples, the imaging system, the illumination system, or both are positioned external to the optical window 204, such as between the optical window 204 and the adjustment mechanism 202 or in a cavity in the adjustment mechanism 202. Visible or infrared light is transmitted through the optical window 204 to enable imaging of the environment in the vicinity of the distal face of the optical window 204.

An instrument delivery channel 212 is defined through the optical finger 206. The instrument delivery channel 212 is aligned with the instrument delivery channel defined through the sheath 104, such that an interventional instrument can be delivered through the optical finger 206 and protrude from the distal face of the optical finger 206. For instance, tissue can be grasped between the optical finger 206 and the grasping finger 208, and the interventional instrument can be delivered through the instrument delivery channel 212 to perform a procedure on the grasped tissue.

In the example of FIG. 2, the grasping finger 208 is circular and with an open central region, and the inner diameter of the grasping finger 208 is larger than the outer diameter of the optical finger 206. To open the grasping tool 102, the optical finger 206 is withdrawn (e.g., translated proximally toward the sheath 104) relative to the grasping finger 208 such that a gap is formed between the optical finger 206 and the grasping finger 208. When tissue to be grasped (e.g., a leaflet in a mitral valve or tricuspid valve) is positioned between the optical finger 206 and the grasping finger 208, the optical finger 206 can be translated distally relative to the grasping finger 208 to close the system, reducing or eliminating the gap between the optical finger 206 and the grasping finger 208. Upon closure of the system, the tissue is pressed between the optical window 204 into the grasping finger 208 such that the position of the tissue is stabilized relative to the grasping tool 102, e.g., facilitating performance of an interventional procedure. In the example of FIG. 2, the grasping tool 102 is in a closed position, and the grasping finger 208 and the optical window 204 are concentric with respect to a cross-sectional plane of the optical window 204. In some examples, the grasping finger 208 remains distally forward of the distal face of the optical window 204 when the grasping tool 200 is in a closed position. In some implementations, instead of the optical finger 206 translating proximally and distally relative to the grasping finger 208 to open and close the system, respectively, the grasping finger 208 translates distally and proximally relative to the optical finger 206 to open and close the system, respectively. In some implementations, both the grasping finger 208 and the optical finger 206 can be translated.

In some implementations, the grasping finger 208 can be a semi-circle (e.g., rather than the complete circle of FIG. 2). In some implementations, the grasping finger 208 can be a solid or mesh disk (e.g., without the opening in the center of the circle as shown in FIG. 2). The disk can be formed of a transparent or mesh material that provides traction to facilitate gripping of tissue while also enabling visualization of the environment in the vicinity of the distal tip of the system.

In the example of FIG. 2, the grasping finger 208 is attached to the housing 210 by a support element 216. The housing 210, support element 216, and grasping finger 208 can be a single, integral element or can be multiple elements attached to one another. In the example of FIG. 2, the housing 210 houses, e.g., encloses a proximal portion of the optical finger 206. In some examples, the optical finger 206 is entirely outside of the housing 210. The housing 210 can be configured to provide a generally smooth outer surface to contact the body and internal tissues. The housing 210 is attached to the sheath 104. When the housing 210 is attached to the sheath 104, the tube in the sheath 104 that defines the instrument delivery channel extends beyond a distal tip of the sheath 104 and through the housing 210. The instrument delivery channel 212 in the optical finger 206 aligns with the tube that extends through the sheath 214 and housing 210 such that an interventional instrument can pass through the optical finger 206 and protrude from the distal face of the optical finger 206.

In the example of FIG. 2, the grasping finger 208 is rigidly attached to the housing 210 such that the position of the grasping finger 208 is fixed relative to the housing while the optical finger 206 can be translated relative to the housing 210. In some implementations, the optical finger 206 is rigidly attached to the housing 210 the position of the optical finger 206 is fixed relative to the housing 210 while the grasping finger 208 can be translated relative to the housing 210. The housing 210 can house electrical wires or other control or signal elements.

Figure 3:
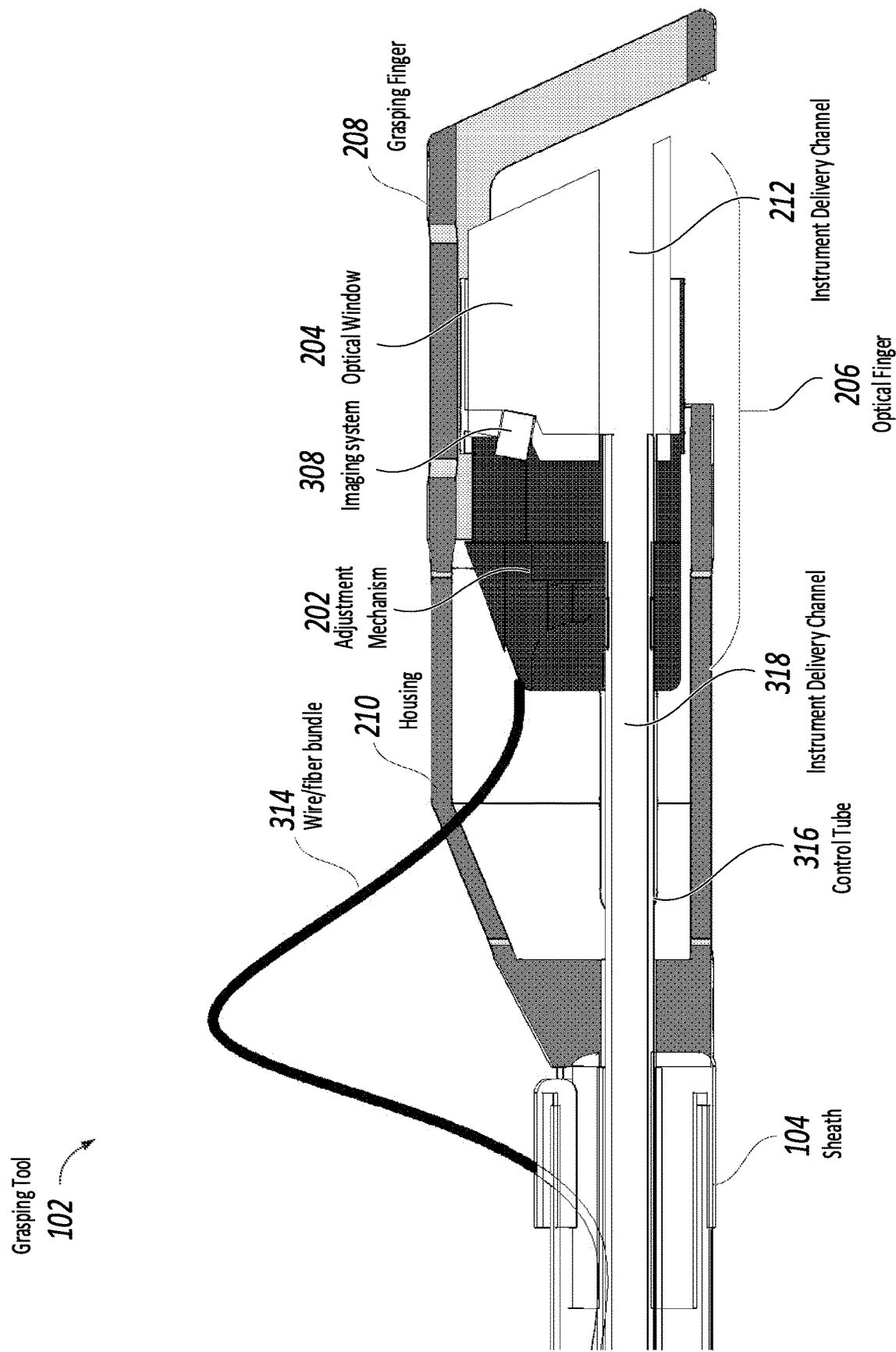
FIG. 3 is a cutaway diagram depicting a system for delivering interventional instruments.

FIG. 3 shows a detailed cutaway diagram of the grasping tool 102. The optical finger 206 includes an optical system including an imaging system 308 (e.g., a camera, as shown, or optical fiber) and an illumination system (not shown). The optical window 204 creates an optically transparent (e.g., allows visible or infrared wavelengths of light to pass through) pathway between the imaging system 208 and the environment in the vicinity of the distal face of the optical window 204. For instance, when tissue is positioned between the optical finger 206 and the grasping finger 208, the imaging system 308 can obtain images of the tissue through the transparent material of the optical window 204, e.g., to facilitate grasping of the tissue or performance of an interventional procedure. The optical window 204 displaces the nearly opaque blood that would normally prevent imaging of tissue as well as provides a contact surface with which to grasp the tissue. The optical window described here is a device formed of a transparent polymer having a distal face that can conform to the topology of the tissue, thus displacing blood from the interface between the distal face and the tissue and creating an optically clear path for imaging the tissue.

The optical window 204 can be a solid window formed of a transparent, compliant, biocompatible material, such as a polymer (e.g., silicone, silicone rubber, castable resins such as acrylic resins or polyurethanes, or another polymer), glass, transparent crystals, or another transparent, compliant material. In some instances, the optical window 204 is hollow, and filled with a transparent biocompatible liquid (e.g., saline). The compliance of the optical window 204 can be controlled by the thickness and composition of the polymer and the conditions under which the polymer is processed, such as the curing temperature. The compliance of the optical window 204 helps facilitate contact with and imaging of tissue, and further helps to prevent damage to tissue it contacts. The optical window 204 can be formed of a material having a refractive index that is similar to the refractive index of the environment in which the grasping tool 102 is to be deployed or to a fluid used to flush the instrument delivery channel 212. In a specific example, the optical window 304 is formed of optically clear silicone (QSil 216 or QSil218 RTV-2 silicone rubber, Quantum Silicones LLC, Richmond, Va.) with a refractive index of about 1.4.

As shown in FIG. 3, the adjustment mechanism 202 provides structural support and an overall base shape for the optical finger 206. The adjustment mechanism 202 can be a transparent or opaque metal or polymer having sufficient mechanical integrity to support the optical window 204, imaging system 308, and illumination system (not shown). The adjustment mechanism 202 can provide guide paths or contact elements for wires or fibers 314 (e.g., a wire or fiber bundle) over which power and/or control signals are transmitted to the optical system and image data is transmitted from the optical system. The adjustment mechanism can support structural elements, such as pins, to attach to the housing 210, e.g., to fit in guide slots in the housing 210, to help ensure proper alignment of the optical finger 206 with the grasping finger 2108.

As discussed above, an instrument delivery channel 318 is defined by a control tube 316 that extends through the sheath 104 and beyond the distal tip of the sheath 104 into the housing 210. The control tube 316 rigidly connects to the optical finger 206, e.g., to the the adjustment mechanism 202 such that the instrument delivery channel 212 defined through the optical finger 206 aligns with the instrument delivery channel 218 defined by the control tube 316. The rigid connection between the control tube 316 and the optical finger 206 enables distal or proximal translation of the control tube 316 (e.g., by a practitioner operating the grasp handle 106 (see FIG. 1A) to cause distal or proximal translation of the optical finger 206 relative to the housing 210 and relative to the grasping finger 208. As noted above, in some examples, the control tube 316 is instead rigidly connected to the housing 210 such that motion of the control tube 316 causes motion of the housing 210, and thus of the grasping finger 208, relative to the optical finger 206. In some examples, two concentric control tubes can be provided through the sheath 104, one control tube rigidly attached to the optical finger 206 and the other control tube rigidly attached to the housing 210. In some examples, only one of the two concentric tubes is controllable; in some examples, each tube is independently controllable to enable motion of both the optical finger 206 and the grasping finger 208.

The imaging system 308 can be embedded in a cavity formed in the optical window 204 or disposed external to the optical window 204 (as shown in FIG. 3), e.g., affixed to the adjustment mechanism 306. The imaging system 308 can be, for instance, a charge-coupled device (CCD) camera (e.g., a 5 mm diameter CCD camera) or a complementary metal-oxide semiconductor (CMOS) camera (e.g., a 1 mm×1 mm×1 mm CMOS video camera (250×250 pixels, Naneye, Awaiba, Inc., Funchal, Madeira, Portugal)). The use of a CMOS camera can have advantages. For instance, in a CMOS sensor, each pixel has its own charge-to-voltage conversion, and the sensor often also includes amplifiers, noise-correction, and digitization circuits, so that the chip outputs digital bits. This lowers camera cost while providing faster readout, lower power consumption, higher noise immunity and a smaller system size. The imaging system 308 can be configured to have a field of view that passes through the optical window 204 such that live images of any tissue in contact with the distal face of the optical window 204 can be readily displayed for the practitioner's analysis. In some implementations, the imaging system is a CCD or CMOS imaging system that is located remotely to the grasping tool 102, and an optical fiber bundle is instead positioned to provide a field of view through the optical window 204. In some implementations, the imaging system 308 can capture visible light (e.g. 350-760 nm wavelengths) as well as infrared or near infrared light (e.g., 750-3000 nm wavelengths).

Wire/fiber bundle 314 can contain wires and/or optic fibers to transmit and receive power and/or information from the optical system. The wire/fiber bundle 314 can provide, for example, an electrical power supply to power an illumination system and the imaging system 308, as well as one or more data lines to transmit optical information from the imaging system 308. The imaging data can, for example, then be relayed to and displayed on a display connected to a computing device. In some implementations, the wire/fiber bundle 314 can exit the housing 210 and be disposed external to the sheath 104. In some implementations, the wire/fiber bundle 314 can be entirely contained within the grasping tool 102, and return to the proximal end of the interventional instrument delivery system inside the sheath 104.

The grasping finger 208 and the distal face of the optical finger 206 are provide a backing against which tissue to be grasped (e.g., the leaflet of a cardiac valve) is pressed. In the example of FIG. 3 the grasping finger 208 is a ring, which has an inner diameter that is larger than an external diameter of the optical window 204. In this implementation, the grasping finger 208 can pass over the optical window 204 (e.g., the unobstructed optical window 204 can translate distally through the open central region of the grasping finger 208). In some implementations, the grasping finger 208 can be a solid or mesh disk, e.g., formed of a mesh or a transparent, compliant material similar to that of the optical window 204 such that the field of view of the imaging system 308 is not obstructed by the disk of the grasping finger 208. In some implementations, the grasping finger can itself be an optical finger having an imaging system, an illumination system, or both integrated therein. In the example of FIG. 3, the distal face of both the grasping finger 208 and the optical window 204 are flat and angled relative to the axis of the instrument delivery channel 318, to improve the grasping angle and ease tissue capture of, for example, a leaflet of the mitral valve. In some implementations, the distal faces of the grasping finger 208 and optical window 204 can be perpendicular to the axis of the instrument delivery channel 318. In some implementations, the distal faces of the grasping finger 310 and optical finger 302 can be rounded or pointed.

Figure 4:
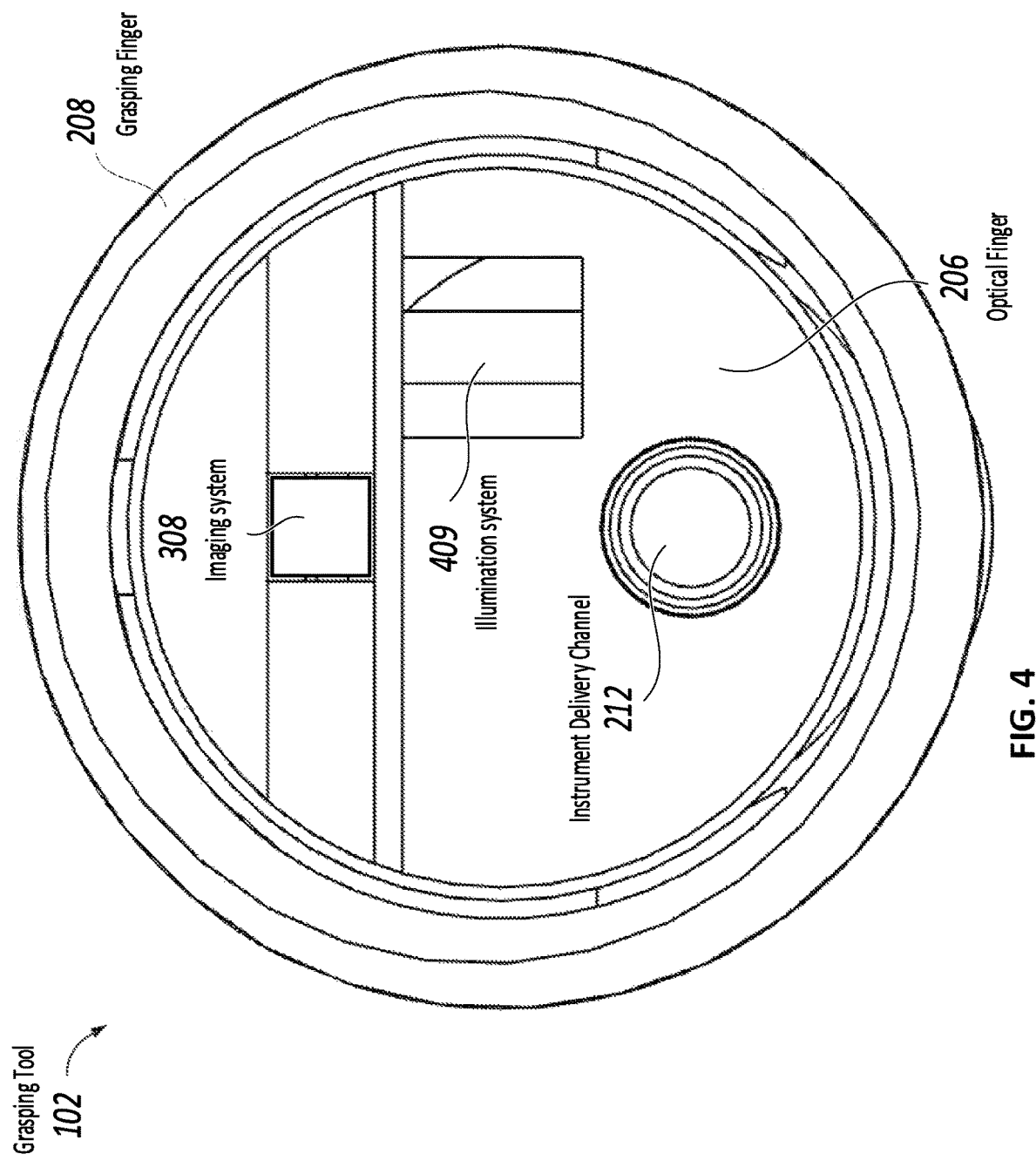
FIG. 4 is a front facing view of a system for delivering interventional instruments.

FIG. 4 shows a front facing view of the grasping tool 102. An illumination system 409 can be embedded in the optical window 204 or disposed external to the optical window. The illumination system 409 is positioned to illuminate an area in the vicinity of the distal face of the optical window 204, e.g., to illuminate an area encompassing the field of view of the imaging system 308. For instance, imaging system 308 and illumination system 409 can be positioned such that the opening of the instrument delivery channel 212 is illuminated and falls within the field of view of the imaging system 308. The illumination system 409 can be a light-emitting diode (LED) or an optical fiber. In one example, the illumination system 409 is a 1.6 mm×1.6 mm LED (Cree Inc., Durham, N.C.). The imaging system 408 and the illumination system 409 can be connected to control electronics or storage devices by way of a wire/fiber bundle, such as the wire/fiber bundle 314 of FIG. 3. In some implementations, the illumination system 409 provides a white light, or emits visible light at a broad range of wavelengths (e.g. 300-700 nm). In some implementations, the illumination system 409 emits light of a particular wavelength, designed to match or be optimal with the parameters of the imaging system 408. For example, if the imaging system 308 is tuned to receive light at near IR wavelengths (e.g., 600-1300 nm) the illumination system 409 can be configured to emit near IR light, at a wavelength where blood is determined to have a lowest absorption rate (e.g., 750 nm or 700-900 nm).

Figure 5A:
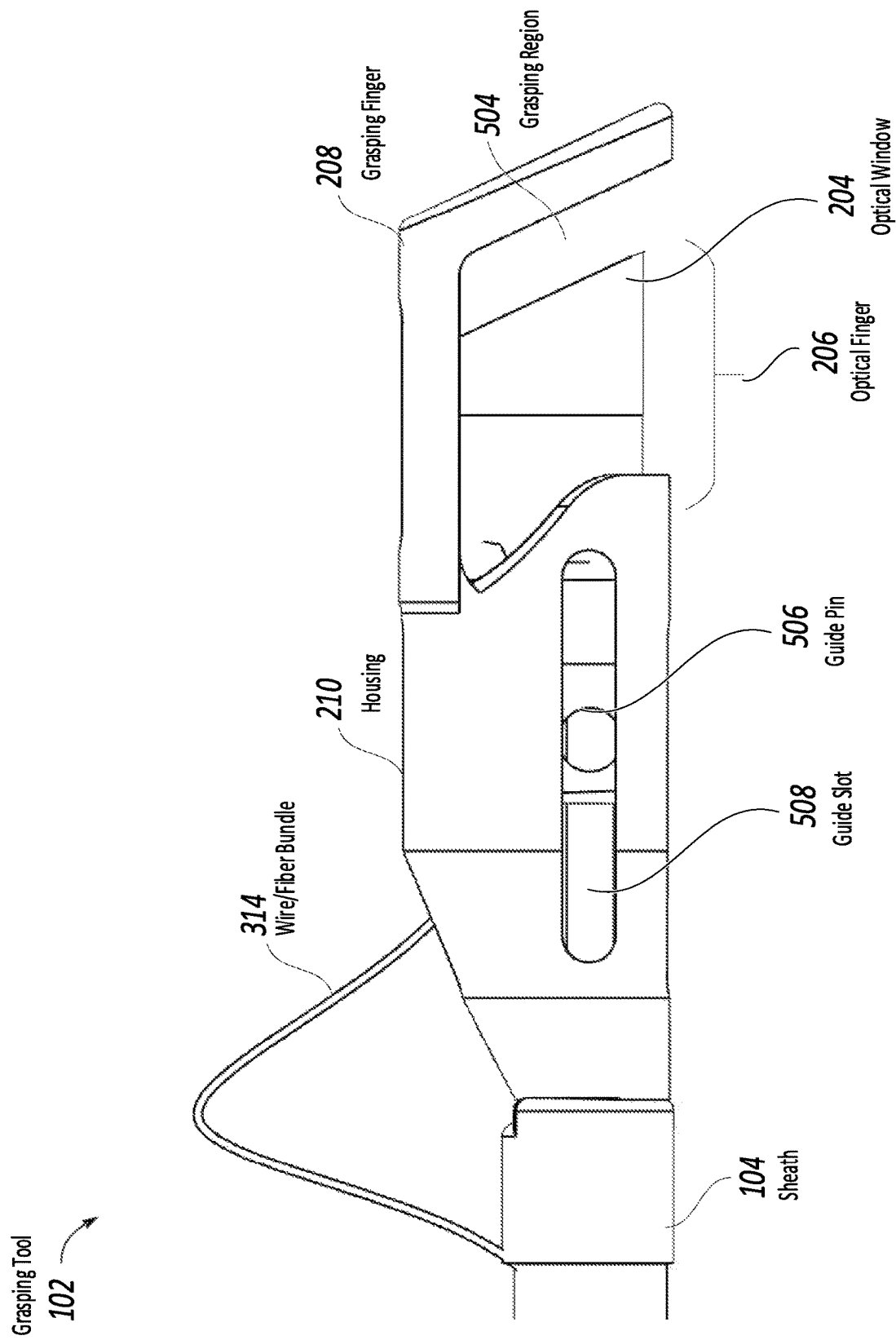
FIG. 5A is a diagram of a system for delivering interventional instruments with grasping finger open.
Figure 5B:
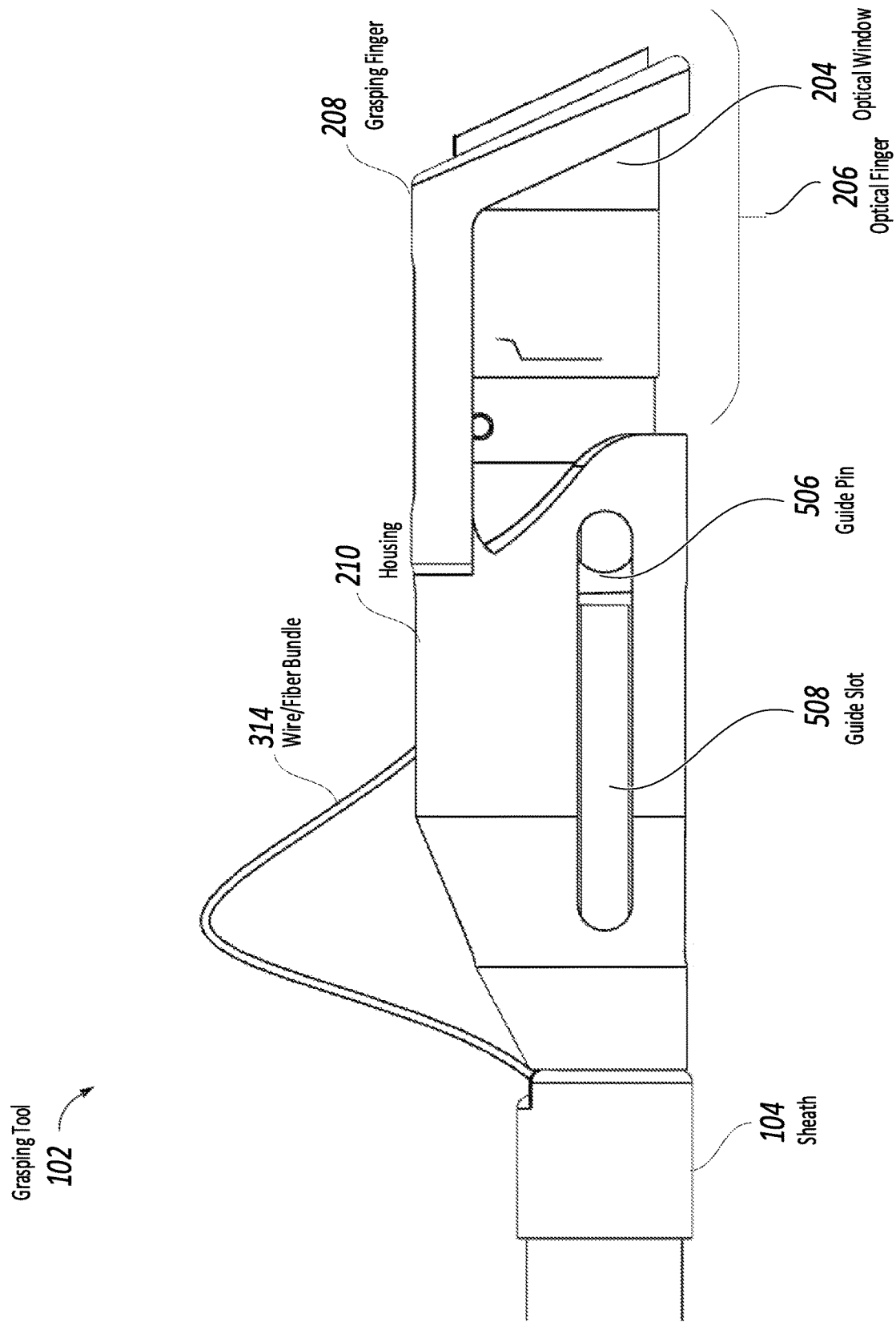
FIG. 5B is a diagram of a system for delivering interventional instruments with grasping finger closed.

FIGS. 5A and 5B show the grasping tool 102 in an open configuration (FIG. 5A) and a closed configuration (FIG. 5B). Referring to FIG. 5A, in the open configuration, the optical finger 206 is partially retracted relative to the grasping finger 208, which leaves a grasping region 504 between the distal face of the optical window 204 and the grasping finger 208. To implement the retraction of the optical finger 206, a guide pin 506 can be attached to the optical finger 206, e.g., attached to the adjustment mechanism of the optical finger 206, and the housing 210 can include a guide slot 508 which provides a track for the guide pin 506 to traverse as the optical finger 206 is retracted proximally or extended distally. In some implementations, the guide pin 506 can be fixed to the housing 512, and the optical finger 206 can include a guide slot 508. The guide slot 508 and guide pin 506 can ensure the optical window 204 and grasping finger 208 are properly aligned. The guide slot 508 and guide pin 506 can limit the range of travel of the optical finger 206, e.g., providing tactile feedback to the practitioner when the optical finger 206 is open or closed. In some implementations, other approaches to aligning the optical window 204 and the grasping finger 208 and to limiting the range of travel of the optical finger 206 can be provided. Wire/fiber bundle 314 can have sufficient slack to allow proximal and distal movement of the optical finger 206 without being damaged or impeding the motion of the optical finger 206. In some implementations, the wire/fiber bundle 314 can be internal to the housing 210. In some implementations, wire/fiber bundle 314 passes out of the housing 210 and then returns into the sheath 104, as shown in FIGS. 5A and 5B. In some implementations, wire/fiber bundle 314 passes out of the housing 210 and remains external along an entire length of the sheath 104.

FIG. 5B shows an example of the grasping tool 102 in a fully closed configuration. The guide pin 506 is translated fully forward in the guide slot 508 and, in this implementation, the optical window 204 passes through the open center of the ring that is the grasping finger 208. If tissue, such as the leaflet of a cardiac valve, were positioned in the grasping region 504 of FIG. 5A when the grasping tool 104 was moved to the closed configuration, the tissue would be grasped between the optical window 204 and the grasping finger 208, and the optical window 204 would not pass through the grasping finger 208 or would pass through to a lesser extent. Although FIG. 5B shows the grasping finger 208 concentric with the optical window 204, in some examples the grasping finger 208 remains distally separate from the optical window 204 even in the fully closed position. In these examples, the width of grasping region 504 is smaller than the width of the grasping region 504 in the open position, which can prevent delicate tissue from being crushed. In some examples, when the system is in the closed configuration, the grasping finger 208 is outside of the field of view of the imaging system so as not to obstruct the imaging of the environment in the vicinity of the distal face of the optical window 204.

In some examples, the grasping tool 102 may be in the fully closed configuration while it is inserted into a beating heart, prior to being used to grasp tissue. By closing the grasping tool 102 during insertion, the chance of abrading or snagging tissue can be reduced. Because the grasping finger 208 does not obstruct the field of view of the optical window, the device can be used to provide optical visualization of an intervention site without ever opening the grasping tool 102. For example, if the tissue of interest is rigid enough that it need not be held in place, the optical window 204 can be pressed against the tissue while the grasping tool 102 is closed, and the interventional instrument can be delivered through the face of the optical window 204.

Figures 6A, 6B:
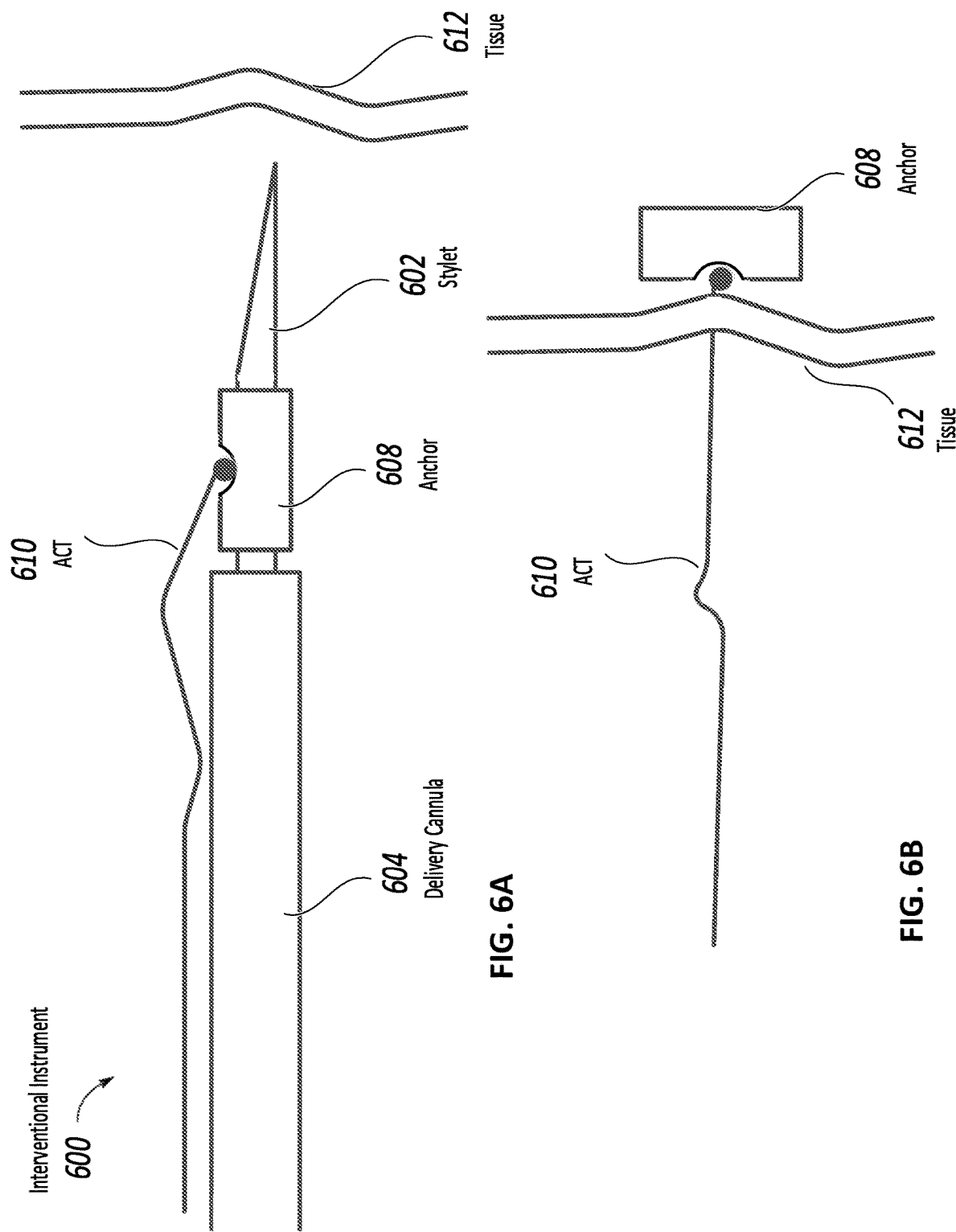
FIG. 6A is a diagram showing an example interventional instrument loaded for delivery.
FIG. 6B is a diagram showing an example interventional instrument deployed in tissue.

FIG. 6A depicts an example interventional instrument. In this example, the interventional instrument is an ACT delivery instrument. The interventional instrument 600 includes a stylet 602, a delivery cannula 604, an anchor 608, and an ACT 610. The entire interventional instrument 600 can be configured to fit within and pass through a channel, such as the instrument delivery channels 318, 212 (see FIG. 3) of the interventional instrument delivery system 102. As the interventional instrument 600 passes through the channels 318, 212 and out of the channel on the distal face of the optical window 204, the stylet 602 can pierce tissue (e.g., tissue 612) that is in the vicinity of, e.g., grasped by the delivery system.

Anchor 608 can be a cylinder, which is configured to fit over the stylet 602, and pass through tissue that the stylet 602 has pierced. Anchor 608 can readily slide off over the tip of the stylet 602, and, as such, if the stylet 602 is then withdrawn through tissue it has pierced, the anchor 608 can slide off and rotate approximately 90 degrees, preventing the anchor 608 from passing back through the tissue as shown in FIG. 6B.

A delivery cannula 604 can house the stylet 602, anchor 608, and ACT 610 while the interventional instrument 600 travels through the delivery system. In some implementations, the anchor 608 has a larger diameter than the inner diameter of the delivery cannula 604, and rests at a distal end of the delivery cannula 604.

The ACT 610 can be a fibrous or synthetic material, such as an expanded polytetrafluoroethylene (ePTFE) material. The ACT 610 can be affixed at a first end to the anchor 608, and can have a free second end, which can be tied off at a predetermined, or adjustable length. In some implementations, the ACT 610 has a second anchor connected to the second end, such that the first anchor, for example, is anchored in a leaflet of a cardiac valve, and the second anchor is anchored in a papillary muscle, or external to the heart.

Figure 7:
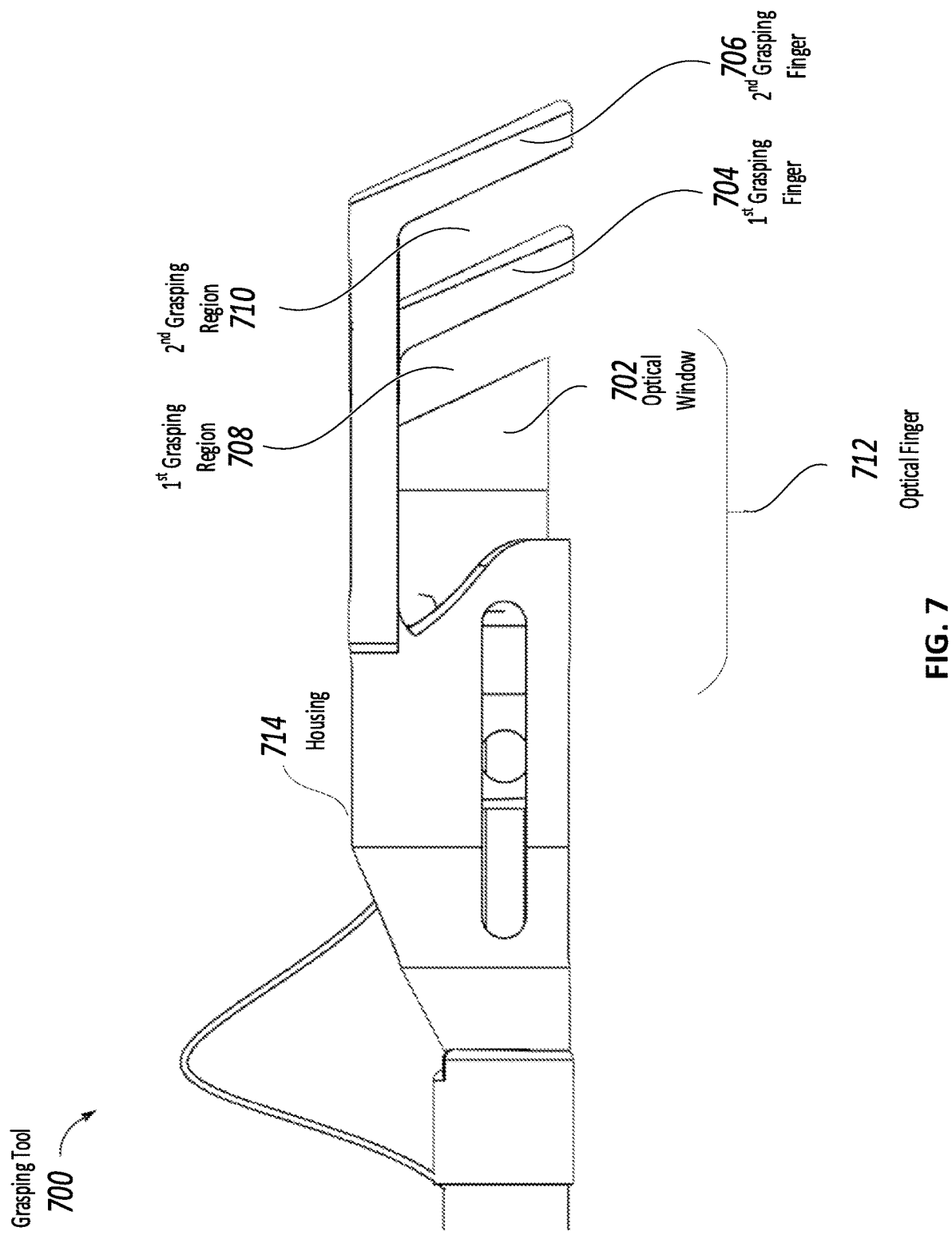
FIG. 7 is a diagram showing an alternate implementation of a system for delivering interventional instruments.

FIG. 7 is a diagram showing an implementation of a system for delivering interventional instruments, with the system including multiple (e.g., two) grasping fingers. FIG. 7 shows grasping tool 700, which can form part of an interventional instrument delivery system. The grasping tool 700 includes two grasping fingers 704, 706 and an optical finger 712 including an optical window 702. In the grasping tool 700, a first grasping finger 704 is translatable independent of the optical finger 712 and a second grasping finger 706, and the second grasping finger 706 is translatable independent of the optical finger 712 and the first grasping finger 704. In some implementations, other combinations of the first grasping finger 704, the second grasping finger 706, and the optical finger 712 are independently translatable. This configuration can create a first grasping region 708 and a second grasping region 710, each of which can be used independently for grasping tissue therein. In some implementations the first grasping finger 704 can slide proximally toward, e.g., become concentric with the optical window 702, thus leaving a single grasping region. In some implementations the first grasping finger 704 can slide distally toward the second grasping finger 706, or the second grasping finger 706 can slide distally toward the first grasping finger 704, thus leaving a single grasping region. The presence of two grasping fingers in grasping tool 700 allows a practitioner to hold multiple pieces of tissue in place (e.g., both leaflets of the mitral valve), e.g., in order to anchor them together, or to verify a tissue quality of multiple tissues.

In the grasping tool 700, the optical finger 712 is mounted to an adjustment mechanism (not shown), e.g., the adjustment mechanism 306 as described with reference to FIG. 3, which is connected to a distal end of a first control tube (not shown). A second control tube can be concentric with the first control tube, and can be affixed at its distal end to the first grasping finger 704. A control lever or slide can be connected to a proximal end of each control tube, to allow both the optical window 702 and the first grasping finger 704 to be translated independently. The position of the second grasping finger 706 is fixed to a housing 714, e.g., the second grasping finger 706 is rigidly connected to the housing 714. In some implementations, the second grasping finger 706 is connected to a third control tube, which is concentric with the first two control tubes, and allows independent translation of the second grasping finger 706. Other combinations of independent translation of one or more of the first grasping finger 704, the second grasping finger 706, and the optical finger 712 can also be implemented by one or more concentric tubes.

Figure 8:
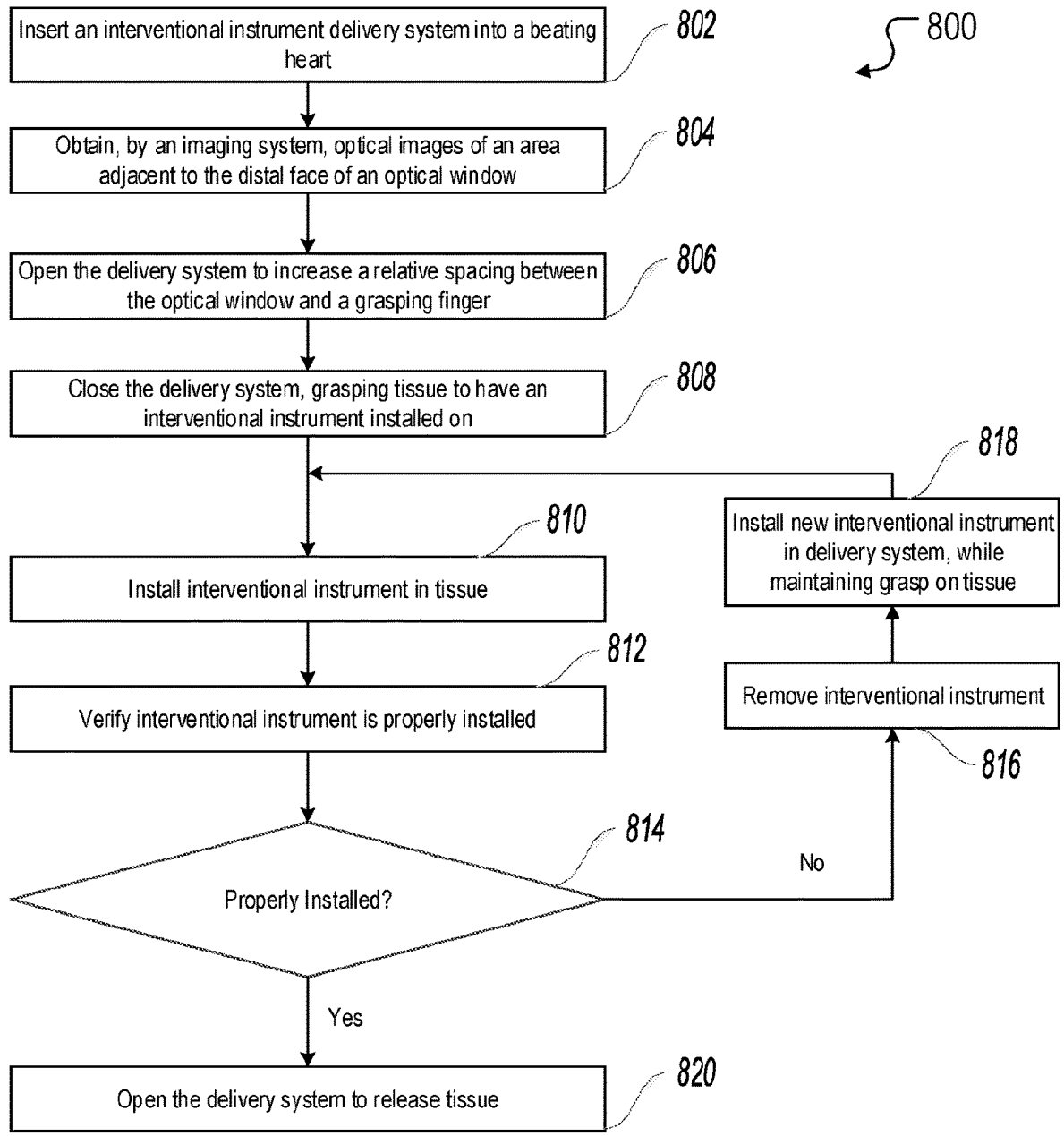
FIG. 8 is a flowchart depicting an example method for using a system for delivering interventional instruments to install an artificial chordae tendinae in a beating heart.

FIG. 8 is a flowchart describing example method 800 for using an interventional instrument delivery system to install an ACT in a beating heart. At 802, the interventional instrument delivery system is inserted into a beating heart. The delivery system can be inserted transapically, transeptally, or by any other suitable means. In some implementations, the delivery system is inserted in a collapsed configuration to enable the delivery system to fit into a small space, e.g., for transvascular delivery.

At 804, once the system is inserted into the heart, optical images can be received from an optical system installed on the distal end of the delivery system. The optical images can be, for example, a live video feed, which a practitioner can use to determine the location of the delivery system, as well as to locate the desired tissue for the installment of an interventional instrument. Once the tissue is located the practitioner can open the delivery instrument. In some examples, when the delivery system is inserted in a collapsed configuration, the delivery system is opened into an expanded configuration upon arrival into the heart and before operating the optical system of the delivery system.

At 806, the delivery system is opened by increasing the space between the optical window of the delivery system and a grasping finger of the delivery system. This can create a grasping region, similar to grasping region 504 as discussed with respect to FIG. 5A. With the delivery system open, the practitioner can adjust the position of the delivery system to place desired tissue in the grasping region and close the delivery system.

At 808, the delivery system is closed, grasping the desired tissue. At this point the practitioner can use the optical images to assess the quality of the tissue, as well as the prospective placement of the interventional instrument. If the tissue quality is determined to be substandard, or a different placement is desired, the practitioner may reopen the delivery system, releasing the tissue, and reposition before closing and re-grasping the tissue in a more desirable location.

At 810, once it is determined that the system is in place, the interventional instrument can be installed. For example, an ACT delivery instrument, similar to the example interventional instrument 600 as described with reference to FIG. 6 can be passed through the delivery system to pierce the tissue and install an anchor and ACT in the grasped tissue. Once the interventional instrument is installed, some or all of the components of the interventional instrument can be removed or partially removed. For example, the stylet and cannula of an ACT delivery instrument can be withdrawn or partially withdrawn.

At 812, using the optical images, the practitioner can verify correct installment of the interventional instrument. For example, if an ACT delivery instrument has the stylet and cannula withdrawn or partially withdrawn, the practitioner may be able to determine if the anchor and ACT are placed correctly, or if the anchor has not properly seated. In the event the interventional instrument is determined to be improperly installed, method 800 can proceed to 816.

At 816, the interventional instrument can be withdrawn through the instrument delivery channel of the delivery system, and at 818, a new interventional instrument can be re-inserted. This can be completed without releasing the grasp of the tissue, and so it is not necessary to relocate a suitable position for installing the interventional instrument. In some implementations, the delivery system is closed into the collapsed configuration for withdrawal.

Returning to 814, if it is determined that the interventional instrument is properly installed, at 820, the delivery system can be opened, releasing its grasp on the tissue, and then removed or relocated to finish installation of the interventional instrument, or to install more interventional instruments.

What is claimed is:

1. A system for delivering an interventional instrument into a beating heart, the system comprising:
    a housing, wherein a first channel is defined through the housing, the first channel configured to receive the interventional instrument; and
    a grasping finger disposed at a distal end of the housing; and
    an optical finger, the optical finger comprising:
        an optical window formed of a transparent material, wherein a second channel is defined through the optical window from a proximal face to a distal face of the optical window, wherein the second channel is aligned with the first channel through the housing; and
        an optical system positioned to obtain optical images of an area adjacent to the distal face of the optical window; and
    wherein the system is configured to take on an open configuration or a closed configuration, wherein a relative spacing between the distal face of the optical window and the grasping finger along an axis defined by the first channel is greater in the open configuration than in the closed configuration.

2. The system of claim 1, wherein the optical system comprises:
    an imaging system positioned to obtain the optical images of the area adjacent to the distal face of the optical window; and
    an illumination system configured to provide illumination to the area adjacent to the distal face of the optical window.

3. The system of claim 1, wherein the optical finger is translatable relative to the grasping finger along the axis defined by the first channel.

4. The system of claim 3, comprising a control tube rigidly connected to the optical finger, wherein the control tube defines the first channel.

5. The system of claim 4, comprising a control handle configured to control a translation of the control tube along the axis defined by the first channel.

6. The system of claim 3, wherein the grasping finger is fixed relative to the housing.

7. The system of claim 1, wherein the grasping finger is translatable relative to the optical finger along the axis defined by the first channel.

8. The system of claim 7, comprising a control tube rigidly connected to the grasping finger.

9. The system of claim 7, wherein the optical finger is fixed relative to the housing.

10. The system of claim 1, wherein the optical finger has a first diameter, and wherein the grasping finger has an inner diameter greater than the first diameter.

11. The system of claim 1, wherein when the system is in the open configuration, the grasping finger is positioned distally forward of the distal face of the optical window along the axis.

12. The system of claim 1, wherein when the system is in the closed configuration, the grasping finger is concentric with a cross-sectional plane of the optical window, and wherein when the system is in the closed configuration, the grasping finger is not present in a field of view of the optical system.

13. The system of claim 1, comprising an elongated sheath, wherein the housing is attached to a distal end of the elongated sheath.

14. The system of claim 1, wherein the transparent material is a compliant, silicone based material.

15. The system of claim 1, wherein the optical window is a hollow optical window that is configured to expand when filled with a liquid.

16. The system of claim 1, comprising an instrument for delivery of leaflet anchors, wherein the instrument is sized to be inserted into the first and second channels.

17. The system of claim 16, wherein the instrument for delivery of the leaflet anchors comprises:
- a stylet, configured to puncture a leaflet in a cardiac valve;
- an anchor, configured to pass through the leaflet and affix a suture to the leaflet; and
- a delivery cannula, wherein the stylet, anchor, suture, and delivery cannula are configured to pass through the first and second channel.

18. The system of claim 1, in which the optical system is embedded in the transparent material of the optical window.

19. The system of claim 1, in which the optical system is disposed between the optical window and the housing.

20. The system of claim 1, in which at least a portion of the optical window falls within a field of view of an imaging system of the optical system.

21. A method for delivering an interventional instrument into a beating heart, the method comprising:
- inserting into a chamber of the beating heart, a delivery system comprising:
  - a housing, wherein a first channel is defined through a length of the housing, the first channel configured to receive the interventional instrument;
  - a grasping finger disposed at a distal end of the housing;
  - an optical finger comprising an optical window formed of a transparent material;
- obtaining, by an optical system of the optical finger, optical images of an area adjacent to a distal face of the optical window;
- opening the delivery system into an open position, including increasing a relative spacing between the distal face of the optical window and the grasping finger along an axis defined by the first channel; and
- closing the delivery system into a closed position, including decreasing the relative spacing between the distal face of the optical window and the grasping finger.

22. The method of claim 21, wherein opening and closing the delivery system comprises translating the optical finger relative to the grasping finger along the axis defined by the first channel, and wherein translating the optical finger relative to the grasping finger comprises moving a control tube along the axis defined by the first channel, the control tube rigidly connected to the optical finger.

23. The method of claim 21, wherein closing the delivery system comprises grasping a leaflet of a cardiac valve, and wherein inserting the delivery system into the chamber of the beating heart comprises inserting the delivery system in a collapsed configuration.

24. The method of claim 21, comprising opening the delivery system into an expanded configuration after inserting the delivery system into the chamber of the beating heart.

* * * * *